(12) United States Patent
Nakamura

(10) Patent No.: US 8,654,191 B2
(45) Date of Patent: Feb. 18, 2014

(54) DEFECT INSPECTION DEVICE AND DEFECT INSPECTION METHOD FOR SILICON WAFER

(75) Inventor: Manabu Nakamura, Kyoto (JP)

(73) Assignee: Nippon Electro-Sensory Devices Corporation, Osaka (JP)

( * ) Notice: Subject to any disclaimer, the term of this patent is extended or adjusted under 35 U.S.C. 154(b) by 287 days.

(21) Appl. No.: 12/451,703

(22) PCT Filed: Dec. 9, 2008

(86) PCT No.: PCT/JP2008/072725
§ 371 (c)(1),
(2), (4) Date: Nov. 25, 2009

(87) PCT Pub. No.: WO2009/157105
PCT Pub. Date: Dec. 30, 2009

(65) Prior Publication Data
US 2010/0165095 A1    Jul. 1, 2010

(30) Foreign Application Priority Data

Jun. 27, 2008   (JP) ................................. 2008-192829

(51) Int. Cl.
*G01N 21/956* (2006.01)
(52) U.S. Cl.
USPC .................... 348/87; 348/92; 438/16; 438/17
(58) Field of Classification Search
USPC ....................................................... 438/16, 17
See application file for complete search history.

(56) References Cited

U.S. PATENT DOCUMENTS

| | | | |
|---|---|---|---|
| 5,196,375 A * | 3/1993 | Hoshi | 438/16 |
| 6,597,444 B1 * | 7/2003 | Halderman et al. | 356/237.1 |
| 7,682,844 B2 * | 3/2010 | Naoe et al. | 438/16 |
| 2007/0178613 A1 * | 8/2007 | Matsumura et al. | 438/17 |
| 2008/0041159 A1 | 2/2008 | Koester et al. | |
| 2011/0025838 A1 * | 2/2011 | Ninomiya | 348/87 |

FOREIGN PATENT DOCUMENTS

| | | | | |
|---|---|---|---|---|
| EP | 2051064 A1 * | 4/2009 | | G01N 21/93 |
| JP | 6-317535 A | 11/1994 | | |
| JP | 08-220008 A | 8/1996 | | |
| JP | 9-311108 A | 12/1997 | | |
| JP | 10-325805 A | 12/1998 | | |
| JP | 11-316179 A | 11/1999 | | |
| JP | 2007-258555 A | 10/2007 | | |
| JP | 2008-003085 A | 1/2008 | | |
| WO | WO-2008-001621 A1 | 1/2008 | | |

OTHER PUBLICATIONS

Machine translation of JP 2007-258555 A.*

* cited by examiner

*Primary Examiner* — Dave Czekaj
*Assistant Examiner* — David N Werner
(74) *Attorney, Agent, or Firm* — Rabin & Berdo, P.C.

(57) ABSTRACT

A defect inspection device for a silicon wafer comprises: an infrared light illumination which illuminates the silicon wafer with a light power that has been adjusted in accordance with a specific resistance value of the silicon wafer; and an imaging unit constituted by a line sensor array that is sensitive to infrared light, which captures the silicon wafer.

10 Claims, 6 Drawing Sheets

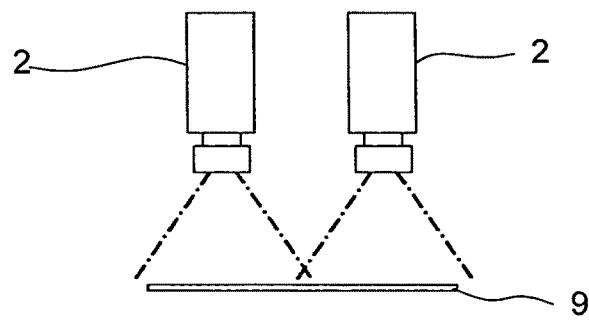
FIG. 5A
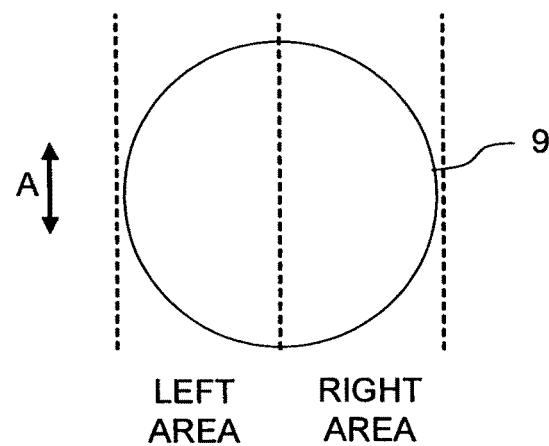
FIG5.B

DEFECT INSPECTION DEVICE AND DEFECT INSPECTION METHOD FOR SILICON WAFER

TECHNICAL FIELD

This invention relates to a defect inspection performed on a silicon wafer, and more particularly to a defect inspection for detecting a surface defect or an interior defect using transmitted light illumination.

BACKGROUND ART

When inspecting a silicon wafer (to be referred to hereafter as a "wafer") used in semiconductor manufacture, a surface inspection for detecting defects on the wafer surface is highly important and is therefore performed with a great deal of care to ensure a zero rejection rate. However, defects in the interior of the wafer have not been accorded much consideration in the prior art.

When a wafer is manufactured, defects (cracks, pinholes, or air bubbles) of several tens to several hundred μm existing in an ingot may be left on the surface or in the interior of the wafer during slicing. When these defects appear on the surface, they can be detected using a surface defect inspection device, but when the defects are left in the interior of the wafer, they cannot be detected by a defect inspection device for performing surface inspections.

Defects such as cracks, pinholes and air bubbles existing in the wafer interior may affect the performance of a semiconductor device, and therefore demand exists for a transmission inspection with which defects in the interior of a wafer can be detected.

DISCLOSURE OF THE INVENTION

A transmission inspection is typically performed on a wafer using infrared light illumination. When infrared light having a wavelength of at least 1100 nm is projected onto the wafer, the light passes through the wafer, and defects in the interior of the wafer can be detected by the transmitted light.

However, with respect to a low resistance wafer having a specific resistance value of 1 Ω·cm or less, the infrared light power that passes through the wafer varies according to the specific resistance value. Therefore, in order to obtain a transmitted light power required for imaging, infrared light illumination must be performed such that the required transmitted light power is secured while taking into account the specific resistance of the low resistance wafer.

Meanwhile, a device that detects defects in the interior of a wafer using an area sensor camera is known as an imaging unit for detecting defects in the interior of a wafer. In this device, an imaging range of the area sensor camera in which a sufficient resolution for the area sensor camera can be obtained is set as a unit area Defects are then detected in the entire wafer by dividing an area of a defect in the wafer interior into these unit areas and moving an imaging position sequentially to obtain a plurality of captured images.

However, when imaging is performed using an area sensor, it is difficult to illuminate all of the unit areas evenly. Unevenness occurs on the captured image between a central portion and an outer edge portion of an imaging area, making it difficult to capture an accurate image. Furthermore, since the inspection is performed by capturing an image in each of a plurality of areas, problems occur in relation to precision and repeatability. Moreover, since the inspection is performed by capturing an image in each of a plurality of small areas, the inspection time lengthens, making it impossible to increase the speed of the inspection process.

According to one aspect of this invention, a defect inspection device for a silicon wafer includes an infrared light illumination which adjusts its light power in accordance with a specific resistance value of the silicon wafer and illuminates the silicon wafer; and an imaging unit constituted by a line sensor array that is sensitive to infrared light, which captures the silicon wafer.

According to another aspect of this invention, in a defect inspection method for a silicon wafer, a light power of an infrared light illumination is adjusted in accordance with a specific resistance value of the silicon wafer, the silicon wafer is illuminated by the infrared light illumination, and the silicon wafer is captured by an imaging unit constituted by a line sensor array that is sensitive to infrared light.

Embodiments and advantages of this invention will be described in detail below with reference to the attached drawings.

BRIEF DESCRIPTION OF THE DRAWINGS

FIGS. 5A and 5B are views illustrating imaging areas of respective imaging units.

BEST MODES FOR CARRYING OUT THE INVENTION

Embodiments of this invention will be described in detail with reference to the drawings. It should be noted that the technical scope of this invention is not limited to the specific constitutions of the embodiments.

Figure 1:
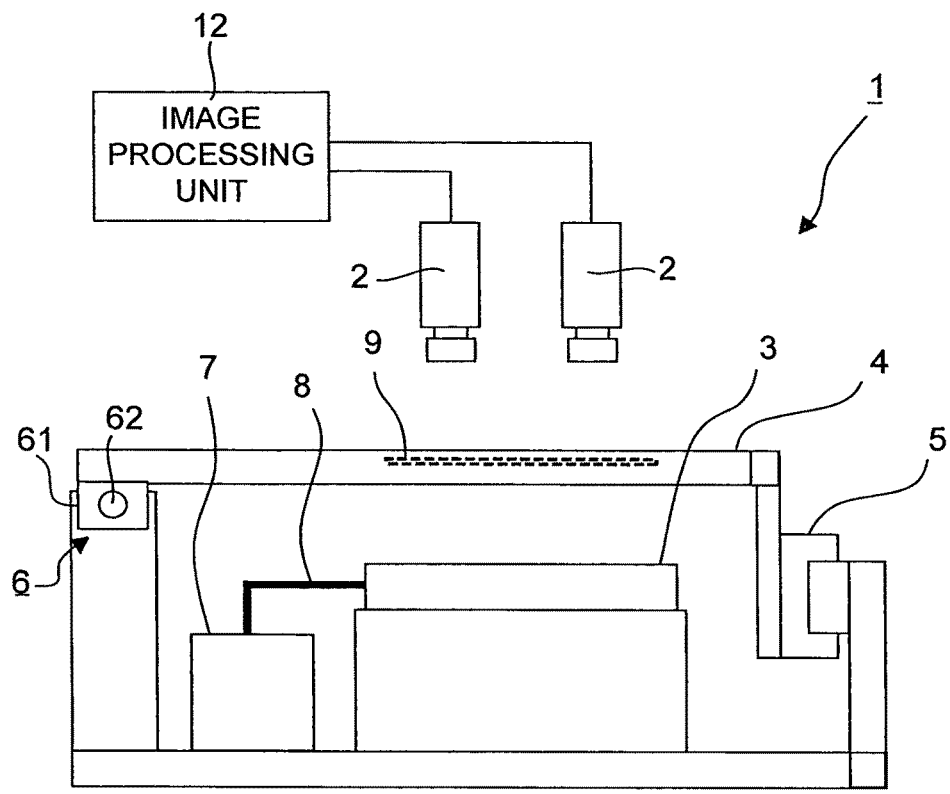
FIG. 1 is a front view of a defect inspection device according to an embodiment of this invention.
Figure 2:
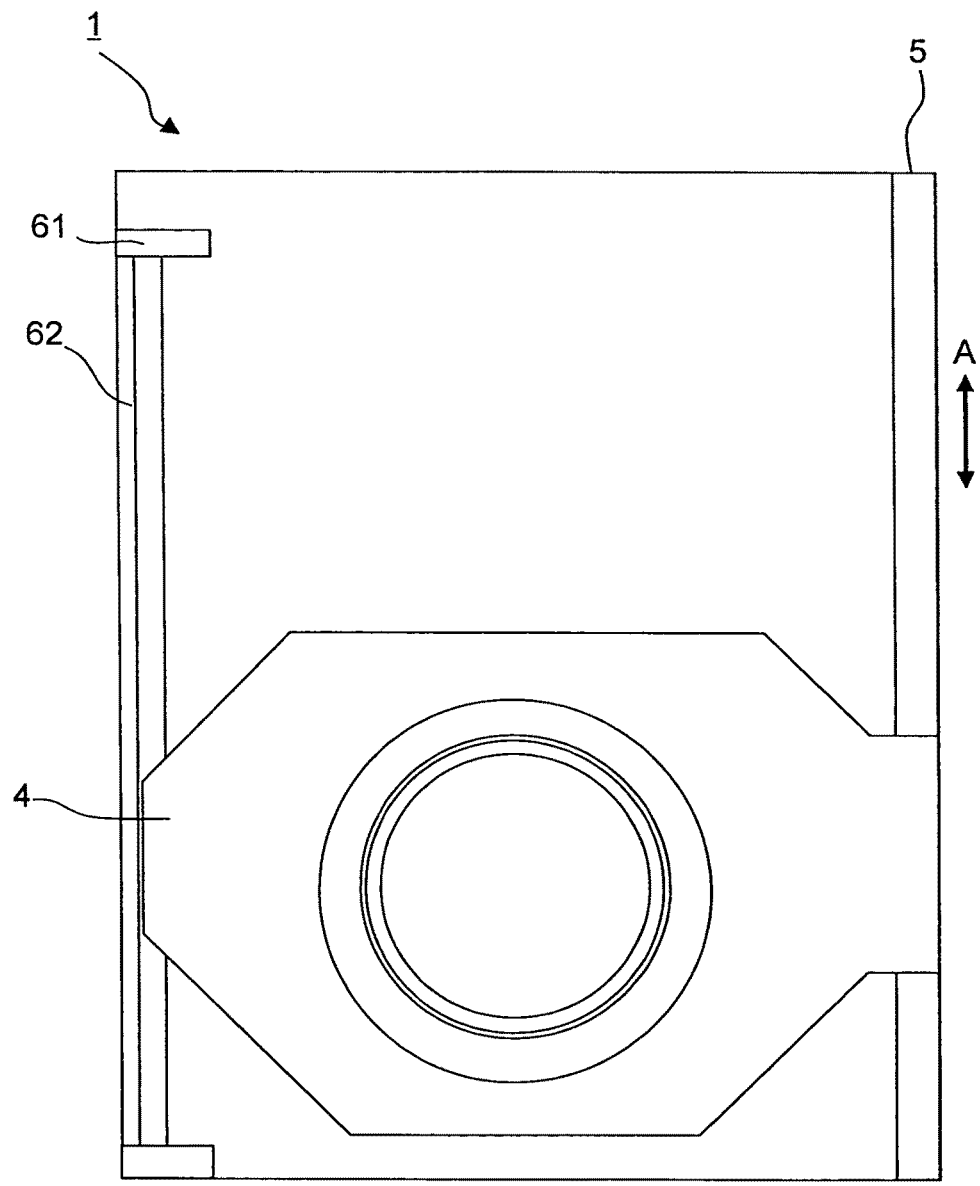
FIG. 2 is a plan view of the defect inspection device.
Figure 3:
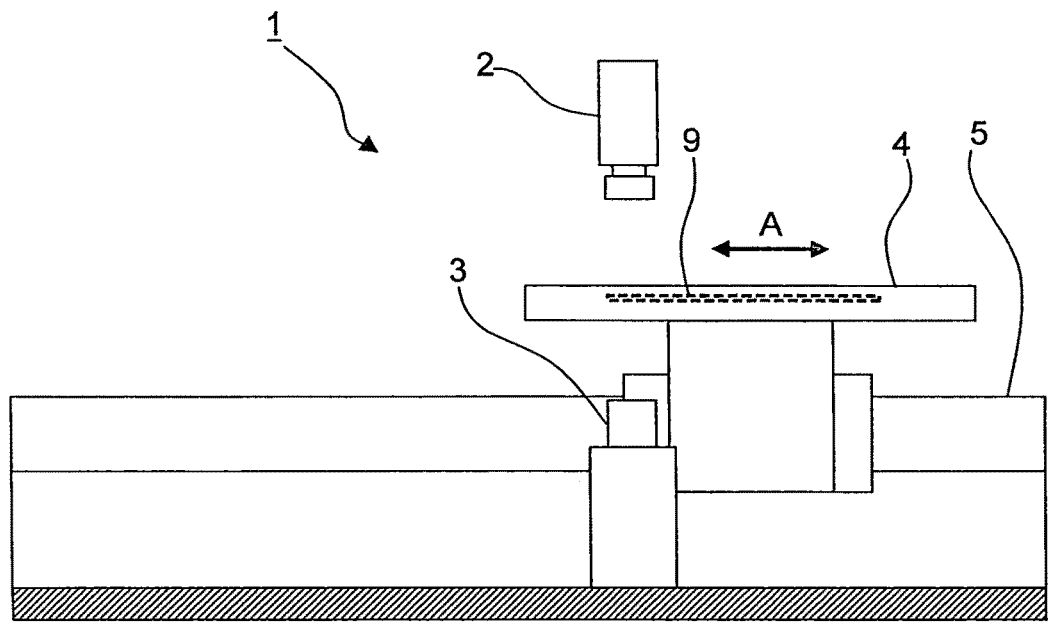
FIG. 3 is a side view of the defect inspection device.
Figure 4:
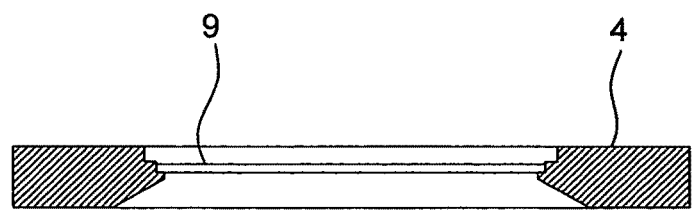
FIG. 4 is a sectional view of a wafer carrying table.

FIGS. 1 to 3 are a front view, a plan view and a side view of a defect inspection device 1 according to an embodiment of this invention. The defect inspection device 1 comprises an imaging unit 2, a line type light guiding exit port (corresponding to an "infrared light illumination", to be referred to hereafter as an "illumination) 3 that emits strip-form infrared light, a wafer carrying table 4, and an image processing unit 12. As shown in FIG. 4, a wafer 9 is carried horizontally on the wafer carrying table 4.

The imaging unit 2 comprises a line sensor array as an imaging device. As shown in FIG. 1, the imaging unit 2 is disposed above the wafer 9 placed on the wafer carrying table 4. The line sensor array used in this embodiment employs high-resolution elements so that even fine flaws and defects can be detected. In the line sensor array, pixels are arranged linearly to provide a scanning function. To obtain a two-dimensional image using the line sensor array, an inspection subject must be moved in an orthogonal direction to a scanning direction of the line sensor array (a pixel arrangement direction). In FIG. 1, the scanning direction of the line sensor array carried on the imaging unit 2 is parallel to the paper surface, and therefore a two-dimensional image can be obtained using the line sensor array by moving the wafer 9, which serves as the inspection subject, in a perpendicular direction to the paper surface (a direction indicated by an arrow A in FIG. 2) using a linear stage 5.

An imaging range is limited by the line sensor array, and therefore an imaging area is divided into a plurality of areas in order to capture an image exceeding this range. An imaging unit 2 for capturing each area is provided, and the respective areas are captured by the line sensor arrays provided in the respective imaging units 2. In this embodiment, as shown in FIGS. 5A and 5B, the imaging area is divided into two areas (a right area and a left area), and a captured image of the entire surface of the wafer 9 is obtained by providing the imaging unit 2 in each imaging area.

A telecentric optical system may be used as the optical system of the imaging unit 2. When a telecentric optical system is employed, the size of the captured image does not vary even if a distance between the imaging subject and the optical system varies, and therefore the position and size of a defect can be grasped accurately.

The wafer 9 does not pass visible light, and therefore transmission observation cannot be performed by normal illumination using visible light. However, the wafer 9 does pass wavelengths greater than 1100 nm (infrared light), making transmission observation possible. Hence, an infrared light source that mainly emits light having a longer wavelength than 1100 nm is used as a light source 7.

The illumination 3 illuminates the imaging area of the wafer 9 serving as the inspection subject in strip form. Infrared light having a longer wavelength than 1100 nm emitted by the light source 7 is emitted onto the wafer 9 from the illumination 3 via an optical fiber 8. The length and width of the illumination 3 used in this embodiment are sufficient to illuminate the imaging area of the imaging unit 2, and by converging the light using a lens, illumination light that is intense enough for imaging can be obtained.

Figure 8:
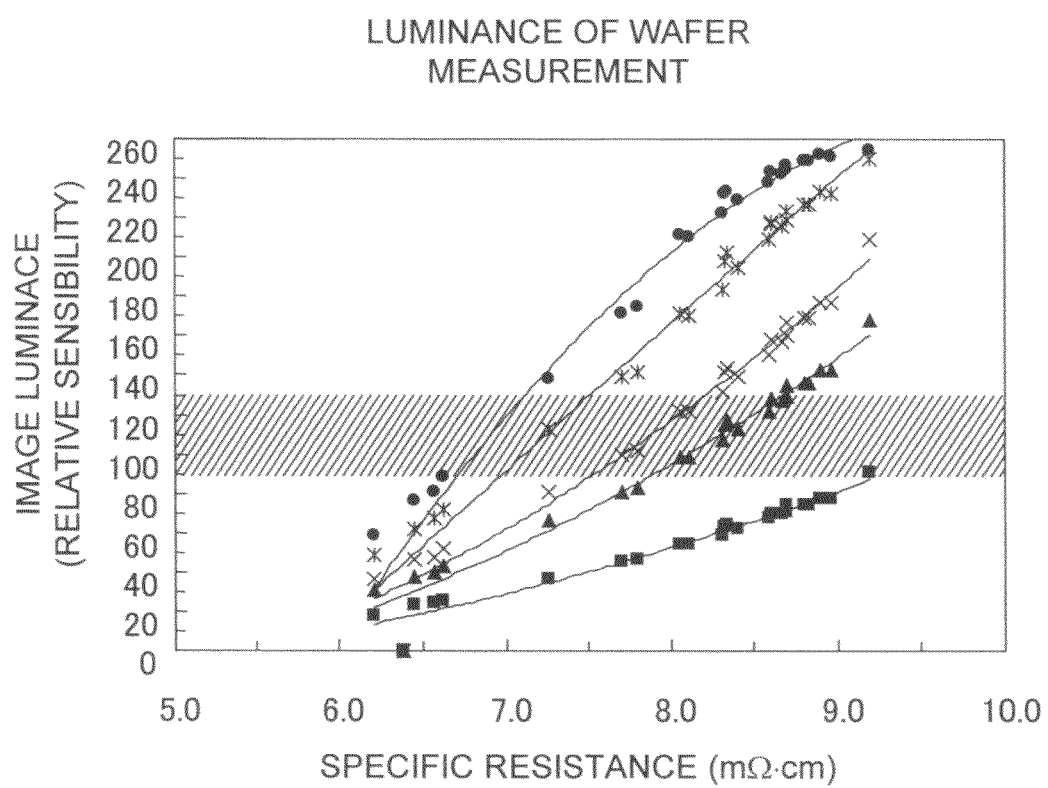
FIG. 8 is a graph showing a relationship between a specific resistance and an image luminance.

FIG. 8 shows a luminance (to be referred to hereafter as "image luminance") obtained when imaging is performed using infrared light passing through the wafer 9 relative to a specific resistance value of the wafer 9. FIG. 8 shows the image luminance of the wafer 9 when the illumination light power (to be referred to hereafter as the "light power") emitted by the illumination 3 is varied. In FIG. 8, the interior of the wafer 9 can be captured appropriately when an image luminance value of the wafer 9 is no smaller than 90 and no greater than 130, and therefore the light power of the illumination 3 is adjusted such that the image luminance of the wafer 9 lies within this range.

In the illumination 3 according to this embodiment, the light power can be set automatically such that the image luminance of the wafer 9 is set appropriately for imaging in relation to the specific resistance of the wafer 9, and thus the light power is set appropriately in accordance with the specific resistance of the wafer 9.

As shown in FIGS. 1 to 3, the wafer carrying table 4 is formed so that it can be moved in the direction of the arrow A by the linear stage 5 and a sliding guide 6. The linear stage 5 is guided by a precision-manufactured rail and a linear guide bearing incorporated into the rail, and includes a driving unit capable of precise positioning. The linear stage 5 moves the wafer carrying table 4 at a constant speed. The sliding guide 6 is constituted by a sliding bush 61 and a sliding shaft 62. The sliding guide 6 supports the load of the wafer carrying table 4, thereby ensuring that the wafer carrying table 4 moves smoothly. In other words, a mechanism for moving the wafer 9 according to this embodiment is constituted by the wafer carrying table 4, the linear stage 5, and the sliding guide 6.

In this embodiment, the wafer 9 is moved relative to the imaging unit 2 and the illumination 3, but the invention is not limited to this constitution, and instead, the imaging unit 2 and illumination 3 may be moved relative to the wafer 9, for example. In this case, the wafer 9 placed on the fixed wafer carrying table 4 is captured while being illuminated, whereby the entire wafer 9 is scanned.

Figure 6:
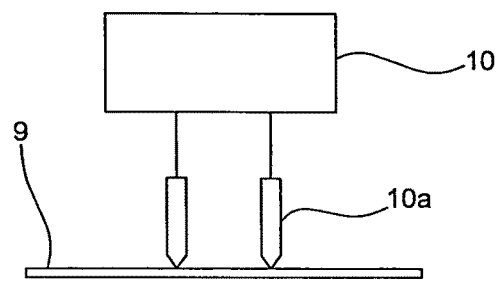
FIG. 6 is a view illustrating the constitution of a specific resistance measurement unit.

FIG. 6 shows the constitution of a specific resistance measurement unit 10 that measures the specific resistance of the wafer 9 during adjustment of the light power of the illumination 3. The specific resistance of the wafer 9 is measured using a measurement probe 10a placed on the surface of the wafer 9. The light power of the illumination 3 is adjusted by adjusting the output of the light source 7 on the basis of the measurement value, and thus the light power passing through the wafer 9 is set at an optimum value for capturing defects in the wafer 9.

Furthermore, in this embodiment, a sensitivity of the imaging unit 2 can be adjusted in accordance with the specific resistance value of the wafer 9. For example, when a sufficient transmitted light power for capturing an appropriate image cannot be obtained simply by adjusting the illumination 3, appropriate image capture is realized by adjusting the sensitivity of the imaging unit 2. In other words, by adjusting both the light power of the illumination 3 and the sensitivity of the imaging unit 2 using the specific resistance value measured by the specific resistance measurement unit 10, an appropriate image luminance for capturing defects can be obtained in relation to the wafer 9.

Next, functions and inspection processes of the defect inspection device 1 according to this embodiment will be described.

The wafer 9 is conveyed by a conveyance device, not shown in the drawings, and placed on the wafer carrying table 4. A wafer holding structure according to this embodiment is a structure for supporting the wafer 9 on a tapered portion provided on the edge of the wafer 9 or an edge portion that does not affect the defect inspection, rather than a structure for gripping the wafer 9 using a gripping device or the like.

The light power of the illumination 3 is adjusted in accordance with the specific resistance value of the wafer 9. By modifying an output of the light source 7 is accordance with the specific resistance value measured by the specific resistance measurement unit 10, the light power of the illumination 3 is adjusted such that an appropriate transmitted light power for imaging is obtained.

The specific resistance value of the wafer 9 is measured by the specific resistance measurement unit 10 shown in FIG. 6. The specific resistance of the wafer 9 may be measured by disposing the specific resistance measurement unit 10 close to the wafer 9 while the wafer 9 is placed on the wafer carrying table 4, or by placing the wafer 9 on a separate carrying table including the specific resistance measurement unit 10 before the wafer is placed on the wafer carrying table 4.

The light power of the illumination 3 is adjusted by modifying the output of the light source 7 in accordance with the specific resistance value of the wafer 9 measured by the specific resistance measurement unit 10. The illumination light emitted by the illumination 3 is adjusted such that the transmitted light power passing through the wafer 9 is sufficient for imaging by the imaging unit 2.

The wafer 9 is moved at a constant speed in a fixed direction by the linear stage 5, and an image generated by the light passing through the wafer 9 is captured by the two imaging units 2. The imaging device carried on the imaging unit 2 is a line sensor array in which pixels are arranged linearly, and therefore a two-dimensional image is obtained by repeating a scanning operation in which the wafer 9 is moved in a sub-scanning direction (the direction of the arrow A in FIG. 2) at the same time as scanning is performed in a main scanning direction, i.e. the direction in which the respective imaging devices are arranged.

The line sensor array of the imaging unit 2 has a limited imaging range. Therefore a wafer having a diameter of 300 mm, for example, is divided into two imaging areas, as shown in FIGS. 5A and 5B, and imaging is performed by the respectively corresponding imaging units 2.

The illumination light emitted from the illumination 3 adjusted to an optimum light power for imaging passes through the wafer 9 to reach the line sensor array provided on the imaging unit 2. When a crack or an air bubble exists on the surface or in the interior of the wafer 9, the transmitted light refracts in that position, causing a gray scale difference to occur in the image captured by the line sensor array. When a crack exists on the surface or in the interior of the wafer 9, a linear image is obtained, and when an air bubble exists, a circular or ring-shaped image is obtained. The image processing unit 12 performs defect determination on the basis of information relating to the shape and gray scale of the defect image.

The method of adjusting the light power of the illumination 3 is not limited to a method of adjusting the light power in accordance with the specific resistance value measured by the specific resistance measurement unit 10, as described above. In a case where the specific resistance has been measured in a previous process, the value thereof may be turned into data for each wafer and stored such that the light power of the illumination 3 is adjusted in accordance with the value. For example, the specific resistance value of the wafer 9 conveyed to the defect inspection device 1 is stored in a storage device, not shown in the drawings, such that when the wafer 9 is transferred to the defect inspection device 1, the value of the wafer 9 is extracted from the storage device and the output of the light source 7 is adjusted on the basis of the value. Thus, the light power of the illumination 3 is adjusted such that the light power passing through the wafer 9 is set at an optimum light power for capturing defects in the wafer 9.

With this method, there is no need to provide the specific resistance measurement unit 10 in the defect inspection device 1. Furthermore, the light power of the illumination 3 can be optimized for imaging before the wafer 9 is transferred, thereby reducing the amount of time required for the inspection.

Further, the sensitivity of the imaging unit 2 can be adjusted in accordance with the specific resistance value of the wafer 9, and by adjusting both the light power of the illumination 3 and the sensitivity of the imaging unit 2 using a specific resistance value measured in advance, an appropriate image luminance for capturing defects can be obtained in relation to the wafer 9.

Figure 7:
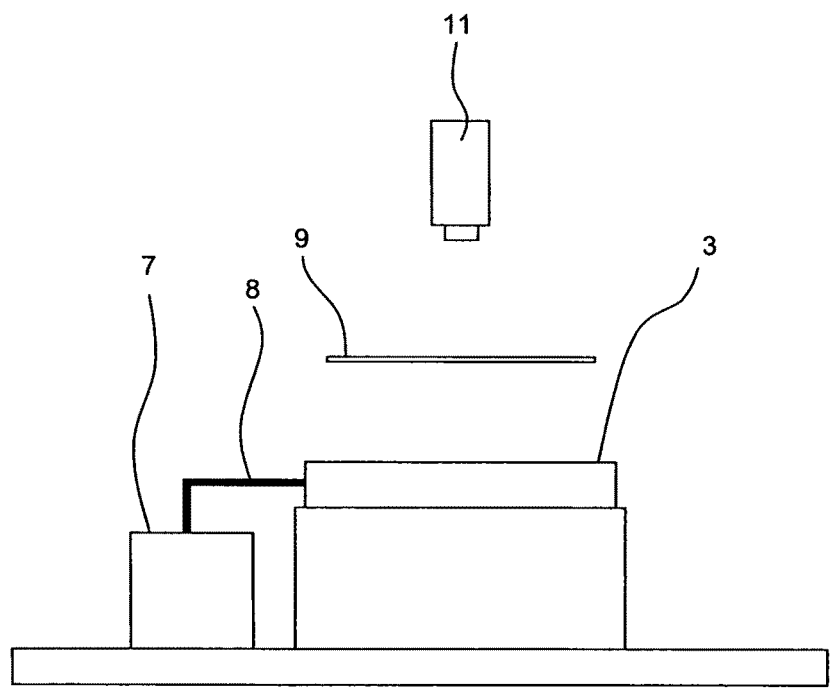
FIG. 7 is a view illustrating the constitution of a transmitted light power measurement unit.

Further, FIG. 7 shows an example in which a transmitted light power measurement unit 11 that measures the transmitted light power passing through the wafer 9 during illumination by an infrared light illumination unit such as the illumination 3 is provided. The transmitted light power measured by the transmitted light power measurement unit 11 is closely related to the image luminance of the wafer 9 such that when the transmitted light power is large, the image luminance of the wafer 9 is high and when the transmitted light power is small, the image luminance of the wafer 9 is low. Hence, the light power of the illumination 3 may be adjusted using the value of the light power passing through the wafer 9. The illumination 3 may be used as the infrared light illumination employed at this time, but the invention is not limited to this constitution, and dedicated illumination for measuring the transmitted light power may be provided instead.

Further, the sensitivity of the imaging unit 2 can be adjusted in accordance with the specific resistance value of the wafer 9, and by adjusting both the light power of the illumination 3 and the sensitivity of the imaging unit 2 using the value of the light power passing through the wafer 9, an appropriate image luminance for capturing defects can be obtained in relation to the wafer 9.

It should be noted that as methods of adjusting the light power of the illumination 3, a method employing the measurement value obtained by the dedicated specific resistance measurement unit 10, a method employing a specific resistance value measured in advance, and a method employing the transmitted infrared light power were described above, but the method of adjusting the light power of the illumination 3 is not limited thereto.

In this embodiment, the entire surface of the wafer 9 is covered by the two imaging units 2, but the number of imaging units 2 is not limited to two. The resolution may be improved by disposing a large number of imaging units 2 in series, and in so doing, an even finer inspection image can be obtained.

As described above, the defect inspection device 1 according to this embodiment of the invention employs a line sensor array that is sensitive to infrared light as an imaging device, and can therefore inspect the entire wafer 9 under identical inspection conditions and respond to an increase in the speed of the inspection process. Further, appropriate illumination for capturing defects can be obtained by obtaining the specific resistance value of the wafer 9 and setting the light power of the illumination 3 at a value corresponding to the obtained specific resistance value. As a result, a defect inspection can be performed evenly and at high speed over the entire surface of a low resistance wafer having a large diameter, on which a transmission inspection is conventionally difficult to perform.

This application claims priority based on Japanese Patent Application No. 2008-192829, filed with the Japan Patent Office on Jun. 27, 2008, the entire contents of which are incorporated into this specification by reference.

The invention claimed is:

1. A defect inspection device for a silicon wafer, comprising:
    an infrared light illumination provided opposite a surface of the silicon wafer;
    an imaging unit having a line sensor array that is sensitive to infrared light from the infrared light illumination; and
    an image processing unit which detects a defect on a surface or in an interior of the silicon wafer from an image captured by the imaging unit,
    wherein a specific resistance value of the silicon wafer is obtained in advance,
    before the infrared light illumination illuminates the silicon wafer, both the infrared light illumination adjusts its light power in accordance with the obtained specific resistance value of the silicon wafer and the imaging unit adjusts its sensitivity to infrared light in accordance with the obtained specific resistance value of the silicon wafer.

2. The defect inspection device as defined in claim 1, further comprising a specific resistance measurement unit which measures the specific resistance value of the silicon wafer.

3. The defect inspection device as defined in claim 1, wherein the imaging unit adjusts its sensitivity to infrared light when a sufficient amount of transmitted infrared light power passing through the silicon wafer is not obtained by adjusting the infrared light illumination.

4. The defect inspection device as defined in claim 2, wherein the specific resistance measurement unit obtains the specific resistance value before the infrared light illumination transmits any infrared light to the silicon wafer.

5. The defect inspection device as defined in claim 1, wherein the infrared light illumination automatically sets its light power in accordance with the obtained specific resistance value of the silicon wafer.

6. A defect inspection device for a silicon wafer, comprising:
   an infrared light illumination provided opposite a surface of the silicon wafer;
   an imaging unit having a line sensor array that is sensitive to infrared light from the infrared light illumination;
   a transmitted light power measurement unit which measures a value of a transmitted infrared light power passing through the silicon wafer in advance; and
   an image processing unit which detects a defect on a surface or in an interior of the silicon wafer from an image captured by the imaging unit,
   wherein a specific resistance value of the silicon wafer is obtained in advance,
   before the infrared light illumination illuminates the silicon wafer, the infrared light illumination adjusts its light power in accordance with the obtained specific resistance value of the silicon wafer, and
   further wherein the imaging unit adjusts its sensitivity to infrared light in accordance with the measured value of the transmitted infrared light power passing through the silicon wafer.

7. The defect inspection device as defined in claim 6, further comprising a specific resistance measurement unit which measures the specific resistance value of the silicon wafer.

8. The defect inspection device as defined in claim 6, wherein the imaging unit adjusts its sensitivity to infrared light when a sufficient amount of transmitted infrared light power passing through the silicon wafer is not obtained by adjusting the infrared light illumination.

9. The defect inspection device as defined in claim 7, wherein the specific resistance measurement unit obtains the specific resistance value before the infrared light illumination transmits any infrared light to the silicon wafer.

10. The defect inspection device as defined in claim 6, wherein the infrared light illumination automatically sets its light power in accordance with the obtained specific resistance value of the silicon wafer.

* * * * *